(12) United States Patent
Bodnar

(10) Patent No.: US 6,197,143 B1
(45) Date of Patent: Mar. 6, 2001

(54) BIOPROSTHETIC CONDUITS

(76) Inventor: Endre Bodnar, Crispin House, 12/A South Approach, Moor Park, Northwood, Middlesex, HA6 2ET (GB)

( * ) Notice: Subject to any disclaimer, the term of this patent is extended or adjusted under 35 U.S.C. 154(b) by 0 days.

(21) Appl. No.: 09/178,860

(22) Filed: Oct. 26, 1998

(51) Int. Cl.⁷ .................................................. A61F 2/24

(52) U.S. Cl. .......................... 156/218; 600/36; 623/901; 623/910

(58) Field of Search .................................. 623/2.13, 2.15, 623/2.16, 901, 910; 600/36; 156/218, 93

(56) References Cited

FOREIGN PATENT DOCUMENTS

14114643 * 4/1992 (JP) .

* cited by examiner

Primary Examiner—Michael W. Ball
Assistant Examiner—Barbara J. Musser

(74) Attorney, Agent, or Firm—Gottlieb, Rackman & Reisman, P.C.

(57) ABSTRACT

A method of making a bioprosthetic conduit, comprises the steps of:

(a) taking a cylindrical mould, having circumferentially spaced protuberances which extend radially from the axis;

(b) curving a layer of a biocompatible sheet material around the cylindrical mould, and joining the opposed edges of the layer together along a longitudinal axis, parallel to the axis of the mould to form a tubular layer; and (c) removing the tubular layer from the mould and turning it inside out to form a cylindrical conduit with sinuses, the conduit being fully fixed by a chemical means; after removal or while still on the mould. Where the conduit is required to be valved, in an additional step (d) an outer biocompatible layer is overlaid on the underlying tubular layer to form a superimposed layer, so that the superimposed layer partially covers the protuberances, the superimposed layer is held in place and sealed onto the underlying tubular layer around the protuberances, to form sinuses and cusps or valve flaps, the layers being partially fixed on the mould by a chemical means.

22 Claims, 2 Drawing Sheets

BIOPROSTHETIC CONDUITS

FIELD OF THE INVENTION

The invention relates to a method of making conduits for use as bioprosthetic replacement, or by-pass, cardiac valve conduits.

BACKGROUND OF THE INVENTION

Extracardiac conduits in the form of biological or synthetic tubes are known to be used in cardiac surgery, primarily for the correction of ventricular outflow abnormalities in patients. It is also known in the literature that aorta or pulmonary valves, of human or animal origin, can be used for the replacement of defective cardiac valves. Replacement valves have also been made from pericardium.

For example in Ann. Thorac. Surg. 1995, 60, S200, there is described a method of making a valved conduit from pericardium tissue. The tissue is moulded by folding it over a template, and partially fixing it with glutaraldehyde. The template contains raised areas on both surfaces, which during fixation of the tissue, form protuberances on the outer surface of the tissue, so that when the folded tissue is sutured together, these protuberances form sinuses and cusps. The template is removed and the folded tissue sutured together in such a manner as to form cusps on one side of the tissue layer and sinuses on the other. The tissue is then rolled around an axis perpendicular to the fold line and sutured together to form a tubular structure, so that the cusps are on the inside and form a valve. The conduit is finally fixed with glutaraldehyde. However, since the tissue is sewn together to form the cusps after the template is removed, the cusps and sinuses may be irregular in size and shape. Thus may result in the valve not closing completely when the conduit is formed.

Another method of forming sinuses on a conduit, is by applying pressure to the inside of a conduit, which is surrounded by an external stent, so as to stretch the walls radially outwards through the stent, thus generating protuberances in the walls of the conduit. However, this is not a favourable method of forming sinuses, as the walls of the sinuses tend to be thinner and thus weaker than the main wall of the conduit.

It is believed that the exact shape and configuration of the cusps is important to guard against unnatural distortion of the valve in use, which would impair proper sealing of the valve cusps.

DESCRIPTION OF THE INVENTION

According to the present invention there is provided a method of making a bioprosthetic conduit, comprising the steps of:

(a) taking a cylindrical mould, having circumferentially spaced protuberances which extend radially from the axis;

(b) curving a layer of a biocompatible sheet material around the cylindrical mould, and joining the opposed edges of the layer together along a longitudinal axis, parallel to the axis of the mould to form a tubular layer, and (c) removing the tubular layer from the mould and turning it inside out to form a cylindrical conduit with sinuses, the conduit being fully fixed by a chemical means; after removal or while still on the mould.

Where the conduit is required to be valved, in an additional step (d) an outer biocompatible layer is overlaid on the underlying tubular layer to form a superimposed layer, so that the superimposed layer partially covers the protuberances, the superimposed layer is held in place and sealed onto the underlying tubular layer around the protuberances, to form sinuses and cusps or valve flaps, the layers being partially fixed on the mould by a chemical means.

Preferably, the mould is radially collapsible like, for example, a chuck, an angioplasty balloon, or an apparatus similar to that used to make Chinese paper lanterns. The mould can, for example, be made of wood, rubber, plastic or metal e.g. stainless steel.

Alternatively, the cylindrical mould is made from soluble material that will quickly dissolve when placed in a solvent, leaving the tubular layer of biocompatible material intact.

The biocompatible layer can be made of biological tissue e.g. pericardium, or biocompatible synthetic material e.g. photo-fixable material.

Most preferably, the biocompatible layers are joined with sutures. Where appropriate, the layers can also be joined by heat sealing, whereby by the means for sealing can be automated and pre-programmed, so as to guide the heat sealer along an exact path. Alternatively, the layers are joined together with a fixing glue or staples.

Preferably, the conduit contains valves which are formed by joining an underlying layer with a superimposed layer, along a fixed pattern, and then turning the tubular structure inside out. Alternatively, the conduit is formed without valves, and a separate valve unit is inserted inside the conduit after assembly. Thus, in the step (d), the outer layer can comprise a second piece of biocompatible sheet material which is held in place on the underlying layer while it is sealed in place by suturing or welding around the periphery of that part of each protuberance which overlaid by the outer layer. Most conveniently however, the outer layer may simply be formed by peeling back one end of the tubular layer until it reaches the required position on the mould. In a particular preferred embodiment of the invention, the end of the tube formed by the two layers of material can be reinforced and cushioned by inclusion of an O-shaped ring. The O-shaped ring further facilitates secure attachment of the conduit to the patient's vascular system by padding the area that is being joined, so as to make suturing easier. The ring is conveniently made of synthetic material, for example a biocompatible rubber.

Preferably the tubular layer is slid off the mould and then turned inside out. Alternatively, the layer can be peeled off the mould so that the tubular layer turns inside out whilst being removed off the mould.

BRIEF DESCRIPTION OF THE DRAWINGS

In order that the invention may be fully understood, a preferred embodiment in accordance therewith will now be described with reference to the accompanying drawings, wherein.

DESCRIPTION OF A PREFERRED EMBODIMENT

The invention will now further be described with reference to the figures and to a certain preferred embodiment, it being understood that this is intended to exemplify, and in no way to limit, the invention.

Figure 1:
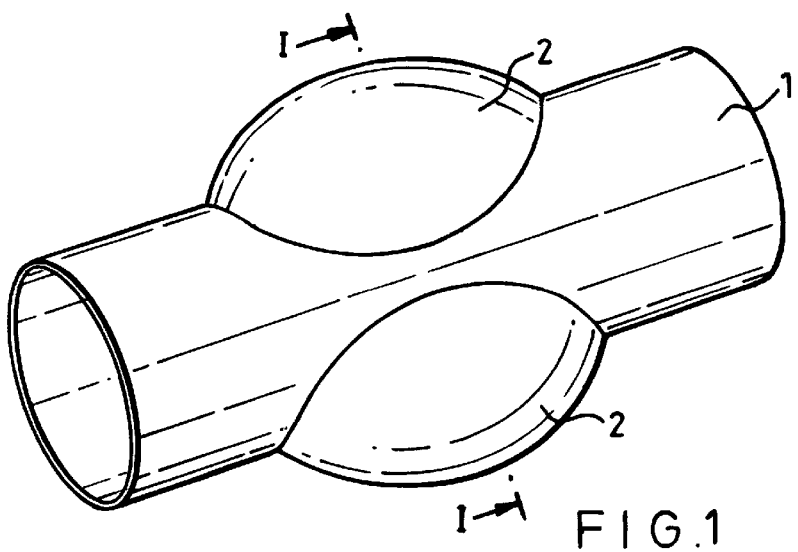
FIG. 1 is a perspective view of the cylindrical mould.
Figure 2:
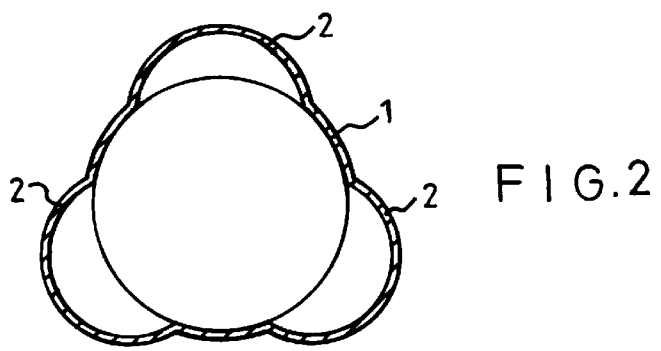
FIG. 2 is an axial view of the mould in cross section.

The cylindrical mould 1 shown in FIG. 1 is provided with three ellipsoidal shaped protuberances 2 (one protuberance is out of view) on the outer surface, the protuberances being evenly radially spaced on the mould, as shown clearly in FIG. 2

Figure 3:
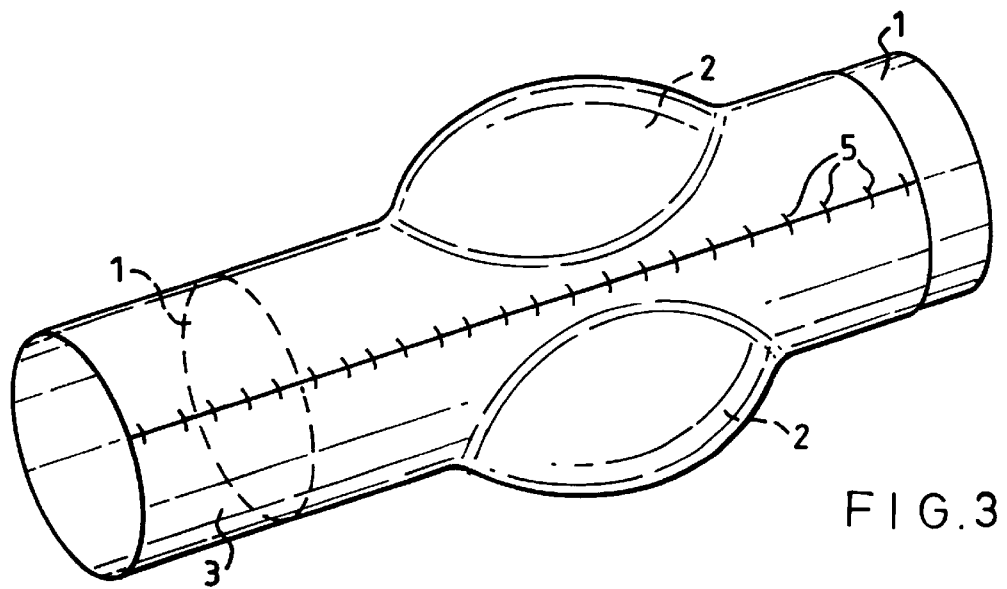
FIG. 3 is a perspective view of a biocompatible layer sutured onto the cylindrical mould.

The opposite edges of the biocompatible layer 3 are sutured 5 together over the mould 1, so that the layer 3 is stretched over the protuberances 2, as shown in FIG. 3.

Figure 4:
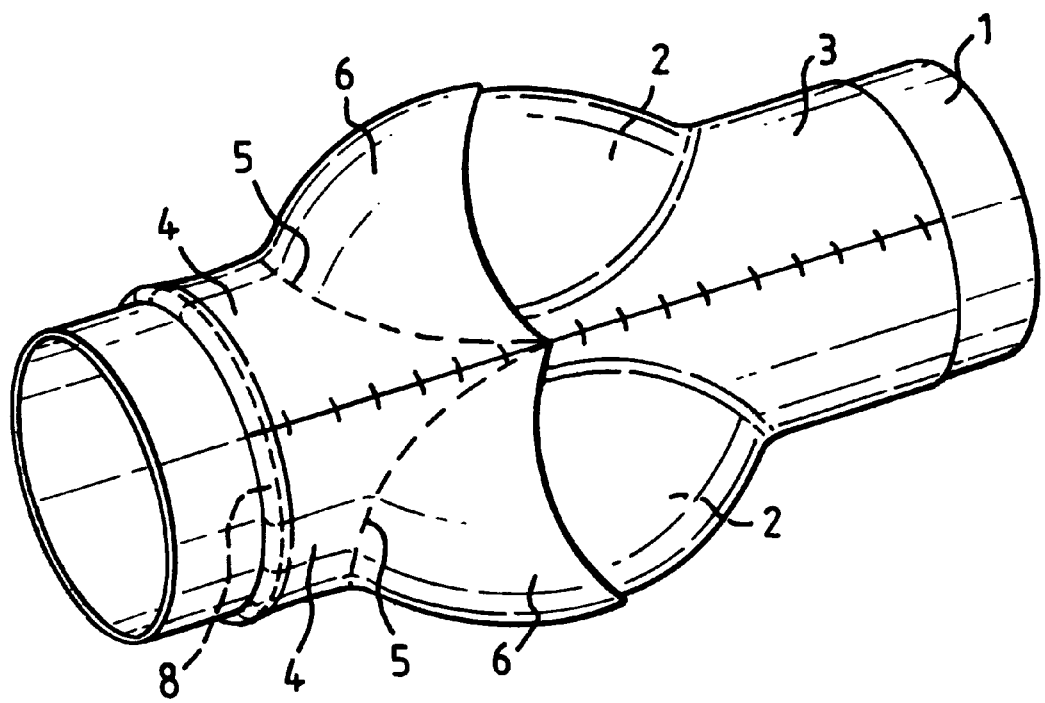
FIG. 4 is a perspective view of the one end of the layer folded back over the mould and sutured.

As shown in FIG. 4, the biocompatible layer 3 is then partially peeled back over the protuberances 2, a synthetic rubber O-ring 8 is inserted in the fold and where necessary, held in position by means of sutures, the superimposed part of the layer 4 being attached to the underlying part of the layer 3 by means of sutures 5, along the peripheries of the protuberances 2, so as to form cusps 6, the cusps having a scalloped configuration (and being at this time, in an inverted configuration).

Figure 5:
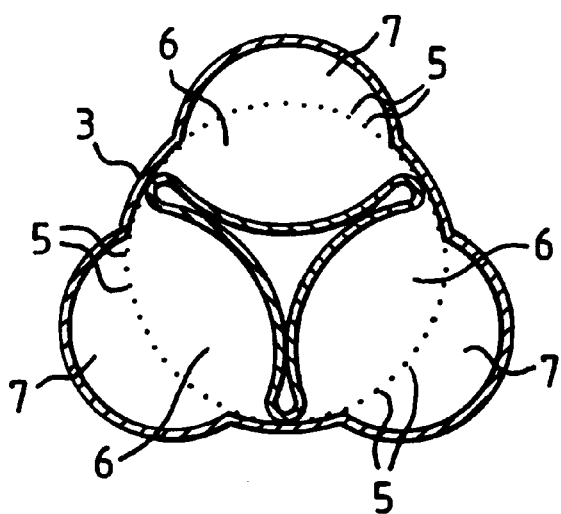
FIG. 5 is an axial view of the conduit in cross-section.

The mould 1 is then collapsed and removed and the tubular layer is turned inside out to form a valved conduit, as shown in FIG. 5. The conduit thus contains three cusps 6 now on the inside, the bases of the cusps 6 attached to the inside wall 3 by means of sutures 5 and three sinuses 7, now on the outside and being part of the outside wall of the tube.

The cusps 6 extend radially from their bases and abut each neighbouring cusp, with their apexes extending radially towards the cylindrical axis of the tubular conduit.

The apex of a cusp 6 can extend radially towards and retract from the axis similarly to the way in which natural valves are permitted to deform reversibly. The conduit also contains sinuses 7 which extend radially away from the axis and comprise the non-folded part of the layer 3. The sinuses are equally circumferentially spaced on the conduit and can retract towards and extend from the central axis during blood flow, similarly to the manner of a natural sinus.

While the description above refers to particular embodiments of the present invention, it will be evident to those skilled in the art that many modifications may be made, and the present invention may be embodied in other specific forms, without departing from the spirit thereof. The present embodiments are therefore to be considered in all respects as illustrative and not restrictive, the scope of the invention being defined by the appended claims, rather than the foregoing description, and all the changes that come within the meaning and range of equivalency of the claims are therefore intended to be embraced therein.

What is claimed is:

1. A method of making a bioprosthetic conduit, comprising the steps of:
   (a) taking a cylindrical mould, having a longitudinal axis, and having circumferentially spaced protuberances which extend radially from said longitudinal axis;
   (b) curving a layer of a biocompatible sheet material around the cylindrical mould, and joining the opposed edges of the layer together along a longitudinal axis, parallel to the longitudinal axis of the mould, to form a tubular layer having protuberances corresponding to those of the mould; and
   (c) removing the tubular layer from the mould and turning it inside out to form a cylindrical conduit, the conduit having sinuses corresponding to the protuberances possessed by the tubular layer whilst still on the mould, and the conduit being fully fixed by a chemical means; after removal or while still on the mould.

2. The method of claim 1, wherein the following additional step is carried out directly after step "b":
   (d) An outer biocompatible layer is curved over the underlying tubular layer to form a superimposed layer, so that the superimposed layer partially covers the protuberances, the superimposed layer is held in place and sealed onto the underlying tubular layer, to form sinuses and cusps or valve flaps, the layers being partially fixed on the mould by a chemical means.

3. The method of claim 2, wherein the additional step (d) is achieved by partially peeling back one end of the tubular layer along the mould, so that the peeled back end partially covers the protuberances, inserting an O-ring of supportive material into the fold, sealing together the superimposed end of the layer and the underlying tubular layer, to form cusps, or valve flaps, and sinuses, the layer being partially fixed on the mould by a chemical means.

4. The method of claim 2, wherein the outer biocompatible layer is a separate layer of biocompatible material, this layer being held in place on the underlying tubular layer and sealed onto the tubular layer.

5. The method of claim 1, wherein the biocompatible layer comprises a synthetic material.

6. The method of claim 1, wherein the tubular mould is radially collapsible.

7. The method of claim 1, wherein the mould is readily soluble.

8. The method of claim 1, wherein the edges of the layer are joined together, or layers sealed together, by a chemical means.

9. The method of claim 8, wherein the chemical means comprises an adhesive.

10. The method of claim 1, wherein the edges of the layer are joined together, or layers sealed together by heat.

11. The method of claim 1, wherein the edges of the layer are joined together, or layers sealed together, by sutures or staples.

12. The method of claim 2, wherein at least one biocompatible layer comprises a synthetic material.

13. The method of claim 2, wherein the tubular mould is radially collapsible.

14. The method of claim 2, wherein the mould is readily soluble.

15. The method of claim 2, wherein the edges of the layer are joined together, or layers sealed together, by a chemical means.

16. The method of claim 15, wherein the chemical means comprises an adhesive.

17. The method of claim 2, wherein the edges of the layer are joined together, or layers sealed together, by heat.

18. The method of claim 2, wherein the edges of the layer are joined together, or layers sealed together, by sutures or staples.

19. The method of claim 1, wherein the biocompatible layer comprises biological tissue.

20. The method of claim 2, wherein at least one biocompatible layer comprises biological tissue.

21. The method of claim 20, wherein the biological tissue is pericardium tissue.

22. The method of claim 19, wherein the biological tissue is pericardium tissue.

* * * * *